US 6,669,339 B2

(12) United States Patent
Nanjyo

(10) Patent No.: US 6,669,339 B2
(45) Date of Patent: Dec. 30, 2003

(54) FUNDUS CAMERA

(75) Inventor: Tsuguo Nanjyo, Toyohashi (JP)

(73) Assignee: Nidek Co., Ltd., Aichi (JP)

( * ) Notice: Subject to any disclaimer, the term of this patent is extended or adjusted under 35 U.S.C. 154(b) by 123 days.

(21) Appl. No.: 09/813,019

(22) Filed: Mar. 21, 2001

(65) Prior Publication Data

US 2001/0024263 A1 Sep. 27, 2001

(30) Foreign Application Priority Data

Mar. 22, 2000 (JP) .......................... 2000-081048

(51) Int. Cl.[7] .................................................. A61B 3/14
(52) U.S. Cl. ...................................... 351/206; 351/211
(58) Field of Search ................................ 351/205, 206, 351/211, 213, 221

(56) References Cited

U.S. PATENT DOCUMENTS

| | | | | |
|---|---|---|---|---|
| 4,279,478 A | * | 7/1981 | Matsumura | 351/206 |
| 4,436,388 A | * | 3/1984 | Takahashi et al. | 351/206 |
| 4,572,627 A | | 2/1986 | Madate et al. | |
| 4,620,779 A | | 11/1986 | Matsumura | |
| 4,743,107 A | * | 5/1988 | Aizu et al. | 351/221 |
| 5,090,416 A | * | 2/1992 | Ogino et al. | 351/216 |
| 5,177,511 A | * | 1/1993 | Feuerstein et al. | 351/205 |
| 5,202,708 A | | 4/1993 | Sasaki et al. | |
| 5,302,988 A | | 4/1994 | Nanjo | |
| 5,543,865 A | * | 8/1996 | Nanjo | 351/206 |
| 5,565,938 A | * | 10/1996 | Hanamura et al. | 351/206 |
| 5,742,374 A | * | 4/1998 | Nanjo et al. | 351/206 |
| 6,139,151 A | * | 10/2000 | Ueno et al. | 351/220 |
| 6,404,985 B1 | * | 6/2002 | Ohtsuka | 351/208 |

FOREIGN PATENT DOCUMENTS

| | | |
|---|---|---|
| JP | 58-89237 | 5/1983 |
| JP | 58-89238 | 5/1983 |
| JP | 63-22823 | 5/1988 |
| JP | 5-15495 | 1/1993 |
| JP | 8-66371 | 3/1996 |
| JP | 10-118030 | 5/1998 |
| JP | 11-104085 | 4/1999 |

* cited by examiner

Primary Examiner—Marvin M. Lateef
Assistant Examiner—John R. Sanders
(74) Attorney, Agent, or Firm—Finnegan, Henderson, Farabow, Garrett & Dunner, L.L.P.

(57) ABSTRACT

A fundus camera having a simplified unit mechanism having a fixation light disposed at a suitable position for efficiently guiding a sight line, the fundus camera comprising an illumination optical system for illuminating a fundus of an eye to be examined with visible illumination light for photographing and with invisible illumination light for observation, a photographing optical system having a first photographic element, for photographing an image of the fundus with visible reflection light from the fundus, an observation optical system having a second photographic element for photographing the image of the fundus with invisible reflection light from the fundus, a wavelength-selecting mirror dividing light into invisible light, a part of visible light, and most of the visible light, a light-dividing member further dividing the optical path of the observation optical system, and a fixation target disposed on the optical path divided from the optical path of the observation optical system by the light-dividing member and at a conjugate position with a photographing surface of the second photographic element.

6 Claims, 3 Drawing Sheets

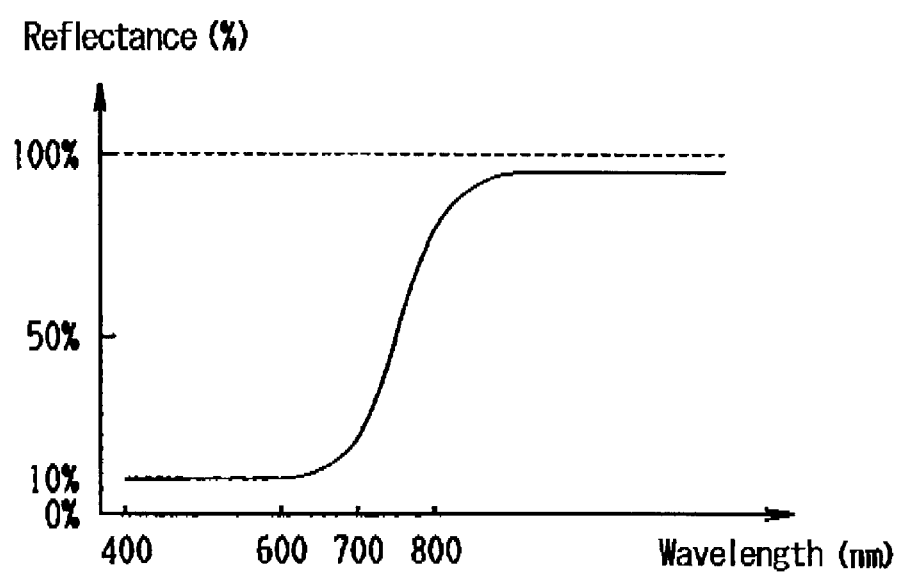
F I G. 2

FUNDUS CAMERA

BACKGROUND OF THE INVENTION

1. Field of the Invention

The present invention relates to a fundus camera for photographing a fundus of an eye to be examined.

2. Description of Related Art

A fundus camera of a non-mydriasis type is well-known to photograph an image of a fundus when an eye to be examined is under a non-mydiasis condition without using mydriatics. Conventionally, as to a fundus camera of the non-mydriasis type, a pop-up mirror having regular mirror coating is used to switch between an optical path of an observation optical system (this optical path may also be referred to simply as an observation optical path, hereinafter) in which the fundus is observed by using infrared light and an optical path of a photographing optical system (this optical path may also be referred to simply as a photographing optical path, hereinafter) in which the fundus is photographed by visible light emitted from a flash lamp or the like.

Also, as to a fundus camera of the non-mydriasis type, it is preferable that a fixation light for guiding a sight line of an examinee be disposed in an optical system thereof. When a fundus camera has a pop-up mirror, it is possible that the fixation light is disposed on the observation optical path switched by the pop-up mirror.

However, in addition to that a mechanism having a pop-up mirror requires a control sequence in which the pop-up mirror synchronizes with a flash lamp and the like and that it complicates a driving mechanism, it has a disadvantage of driving sounds and vibrations at the time of photographing.

Recently, a fundus camera having a dichroic mirror instead of a pop-up mirror to guide visible light to a photographing optical path and infrared light to an observation optical path has been proposed. However, a fixation light emitting visible light is never disposed on the observation optical path divided by using a dichroic mirror. In this structure, though it may be possible that an extra beam splitter is disposed on the photographing optical path, and that a fixation light is disposed on an optical path divided by the beam splitter, it is disadvantageous because light quantity for photographing may decrease. Furthermore, although it is possible that a fixation light is disposed in the same position as a focus index for adjusting the focus, it may be difficult to arrange a mechanism for movement when the fixation light needs to be moved to guide a sight line.

SUMMARY OF THE INVENTION

The present invention has been made in view of the above circumstances and has an object to overcome the above problems and to provide a fundus camera having a simplified unit mechanism, wherein an internal fixation light is disposed at a suitable position for efficiently guiding a sight line.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the present invention, as embodied and broadly described herein, a fundus camera for photographing a fundus of an eye to be examined, the camera comprising an illumination optical system for illuminating the fundus of the eye with visible illumination light for photographing and with invisible illumination light for observation, a photographing optical system having a first photographic element, for photographing an image of the fundus with visible reflection light from the fundus, an observation optical system having a first optical path shared with the photographing optical system, a second optical path divided from an optical path of the photographing optical system by a first wavelength-selecting mirror, a third optical path further divided from the second optical path by a light-dividing member, and a second photographic element disposed on the third optical path, for photographing an image of the fundus with invisible reflection light from the fundus, wherein the first wavelength-selecting mirror has a wavelength-selecting property of transmitting either approximately all of an invisible wavelength range and a part of a visible wavelength range or almost all of the visible wavelength range and reflecting the other, and a fixation target projection optical system having the first optical path, the second optical path, a fourth optical path divided from the third optical path by the light-dividing member, and a light source for eye fixation emitting visible light disposed at a conjugate position with a photographing surface of the second photographic element on the fourth optical path.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

FIG. 2 is a view showing an optical property of a dichroic mirror; and

DETAILED DESCRIPTION OF THE PREFERRED EMBODIMENTS

Figure 1:
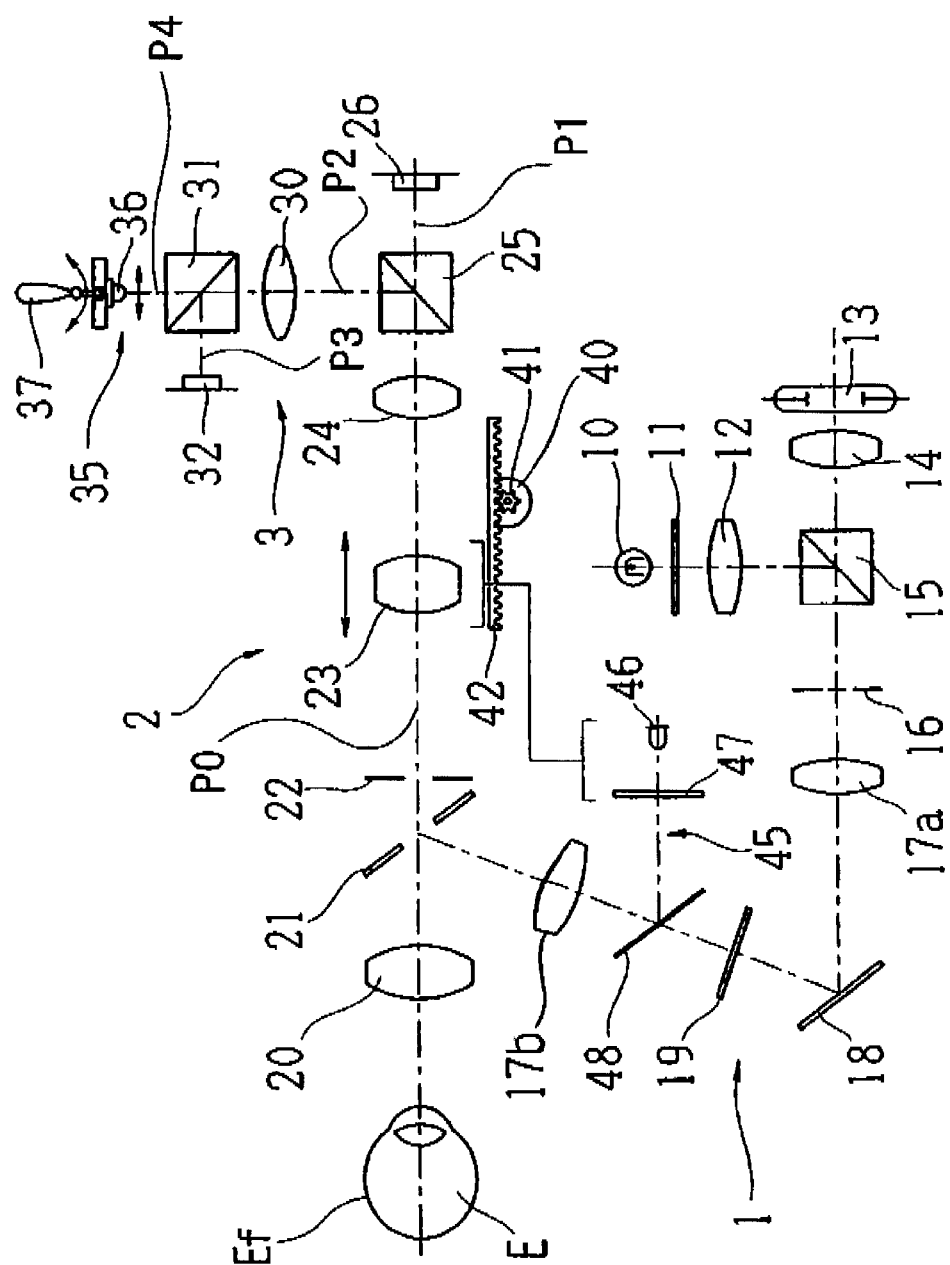
FIG. 1 is a view showing a schematic configuration of an optical system of a fundus camera consistent with a preferred embodiment of the present invention.

A detailed description of one preferred embodiment of a fundus camera embodying the present invention will now be given referring to the accompanying drawings. FIG. 1 is a schematic view of an optical system of the fundus camera of the non-mydriasis type consistent with a preferred embodiment of the present invention. As an optical system, there are provided an illumination optical system 1, a photographing optical system 2, an observation optical system 3, a fixation target projection optical system 35, and a focus index projection optical system 45.

Illumination Optical System

Illumination light emitted from a halogen lamp 10, which is a light source for observation, is changed into infrared illumination light by using an infrared filter 11 having a wavelength-selecting property which transmits infrared light with wavelengths of 750 nm or longer. After passing through a condenser lens 12, the infrared illumination light is reflected by a dichroic mirror 15 having a wavelength-selecting property which reflects infrared light and transmits visible light, and it illuminates a ring slit 16 having a ring-shaped aperture. Instead of the halogen lamp 10, other kinds of infrared light sources, such as an infrared LED and the like, may be used. Under this condition, the filter 11 is not required.

Also, after visible illumination light emitted from a flash lamp 13, which is a light source for photographing, passes through a condenser lens 14, it is transmitted through the dichroic mirror 15 and becomes coaxial with the optical axis of the infrared illumination light to illuminate the ring slit 16.

After passing through the slit 16, the illumination light (ring slit light) forms an intermediate image near an aperture in a mirror 21 with an aperture via a relay lens 17a, a mirror 18, a black dot plate 19 having a small dot on its center, a beam splitter 48, and a relay lens 17b, whereby the light is reflected to be coaxial with the optical axis of the photographing optic system 2. After the illumination light (ring slit light) reflected by the mirror 21 once converges through an objective lens 20 near a pupil of an eye E to be examined, it diffuses to evenly illuminate a fundus Ef of the eye E. When the ring slit light passes through the objective lens 20, a little light is reflected and becomes detrimental light to observing and photographing an image of a fundus Ef, but the detrimental light is absorbed by a small black dot placed in the center of the black dot plate 19.

Photographing Optical System

Reflected light from the fundus Ef passes through the lens 20, the aperture in the mirror 21, a photographic diaphragm 22, a focusing lens 23 which is movable along the optical axis, and an image forming lens 24, and then it enters a dichroic mirror (dichroic prism) 25. As indicated in FIG. 2, the dichroic mirror 25 has a wavelength-selecting property of transmitting about 80% to 90% of visible light with wavelengths ranging from approximately 700 nm to 800 nm and reflecting the residual light accounting for about 20% to 10% as well as most infrared light (reflecting almost all the infrared light with wavelengths of approximately 800 nm or longer). Visible reflection light from the fundus Ef, having passed through the dichroic mirror 25, goes into a color CCD camera 26 for photographing having a sensitivity to the visible range, and an image of the fundus Ef is formed on a photographing surface of the CCD camera 26. A photographed image of the fundus Ef may be used as an electrical image provided that the camera 26 is a high resolution digitized CCD camera having millions of picture elements.

Observation Optical System

The observation optical system 3 shares the elements from the lens 20 to the dichroic mirror 25 with the photographing optical system 2, and an observation optical path P2 is divided from a photographing optical path P1 by the dichroic mirror 25. After infrared reflection light from the fundus Ef reflected by the dichroic mirror 25 passes through a relay lens 30, it is further reflected by a dichroic mirror 31, which has the same wavelength-selecting property as the dichroic mirror 25, so as to enter a CCD camera 32 for observation having a sensitivity to the infrared range. Then, an image of the fundus Ef is formed on its photographing surface.

The lens 23, which is movable along the optical axis of the optical path P0 shared by the photographing optical system 2 and the observation optical system 3, provides a way for adjustment of a refractive error to be consistent with a refractive power of the eye E. The lens 23 is fixedly disposed on a rack 42, and the rack 42 is engaged with a pinion 41 fixedly attached to a rotation axis of a stepping motor 40. The lens 23 moves on the optical axis in conjunction with the rack 42 and the pinion 41 by rotation of the motor 40, and it brings an image of the fundus Ef into focus on the photographing surfaces of the cameras 26 and 32.

Focus Index Projection Optical System

The focus index projection optical system 45 has an index plate 47, an LED 46 emitting infrared light, and a beam splitter 48, and the index plate 47 and the LED 46 move together with the lens 23. After passing through the index plate 47, the infrared light for an index projection is reflected by the beam splitter 48 and the mirror 21 to form an image on a conjugate plane (not illustrated) with the fundus Ef once, and then it is projected into the fundus Ef via the lens 20. As an image of the focus index is projected on the fundus Ef by infrared light, its infrared reflection light is reflected by the dichroic mirrors 25 and 31 and is photographed along with the image of the fundus Ef by the camera 32.

Fixation Target Projection Optical System

The fixation target projection optical system 35 is disposed on the observation optical path P2 side divided from the photographing optical path P1 by the dichroic mirror 25. The dichroic mirror 31 further divides the observation optical path P2 into optical paths P3 and P4, and a fixation light 36 emitting visible light is provided (disposed) on the optical path P4 divided from the optical path P3 on which the camera 32 is provided (disposed). The fixation light 36, disposed at an end of an adjustment knob 37, is arranged to be movable within an approximately conjugate plane with the fundus Ef and the photographing surface of the camera 32. The fixation light 36 is moved within the plane vertical to the projection optical axis as an examiner operates the adjustment knob 37. Accordingly, the position of the fixation light presented to the eye E can be changed, and the fundus Ef can be guided to a desired position for photographing.

Approximately 80% to 90% of the visible light emitted from the fixation light 36 is transmitted through the dichroic mirror 31 and enters the dichroic mirror 25 after passing through the lens 30. Although approximately only 20% to 10% of the visible light (the fixation target) having entered the dichroic mirror 25 is reflected, the visible light proceeds along the shared optical path P0 to be visible to the eye E and to induce eye fixation by the eye E (the visible sensitivity of a human eye is sensitive enough to catch a visible fixation target slightly reflected by the dichroic mirror 25). The brightness of the fixation target to be visible to the eye E may be easily increased by adjusting light quantity of the fixation light 36, and light-dividing members, such as a half mirror, may replace the dichroic mirror 31.

Also, when the fixation light 36 is at a conjugate position with the photographing surface of the camera 32, and when a catoptric system is provided in order that the light from the fixation light 36 forms an image on the photographing surface, an image of the fixation light along with the image of the fundus Ef can be shown on an after-mentioned liquid crystal display (LCD) 53 connected with the output of the camera 32. Accordingly, eye fixation is induced while the movement of the fixation light is observed and operated on the LCD 53.

Although it is mentioned above that the dichroic mirror 25 has a wavelength-selecting property which transmits approximately 80% to 90% of visible light and reflects the residual light, the ratio (proportion) of transmission and reflection is not limited to the specific ratio mentioned above. As it is difficult to completely separate visible light from infrared light considering production of a thin film of a dichroic mirror, a wavelength range of reflected visible light usually remains in a part of a daichroic mirror. Accordingly, the ratio of separating visible light and infrared light may be determined in view of sensitivity of an eye E and a CCD camera and/or of light quantity of the fixation light.

As mentioned above, the fixation target projection optical system 35 has a fixation light embedded on the observation optical path P2 side, which is the optical path of reflected infrared light, by taking advantage of a wavelength range (properties) of reflected visible light remaining (made to remain) in a part of the dichroich mirror 25. Therefore, the embedded fixation light can be visible to the examinee, and the system may be constructed without a driving mechanism to switch optical paths, such as a pop-up mirror. In addition, when a mechanism to move the fixation light for guiding a sight line is used, its arrangement can be simplified.

Figure 3:
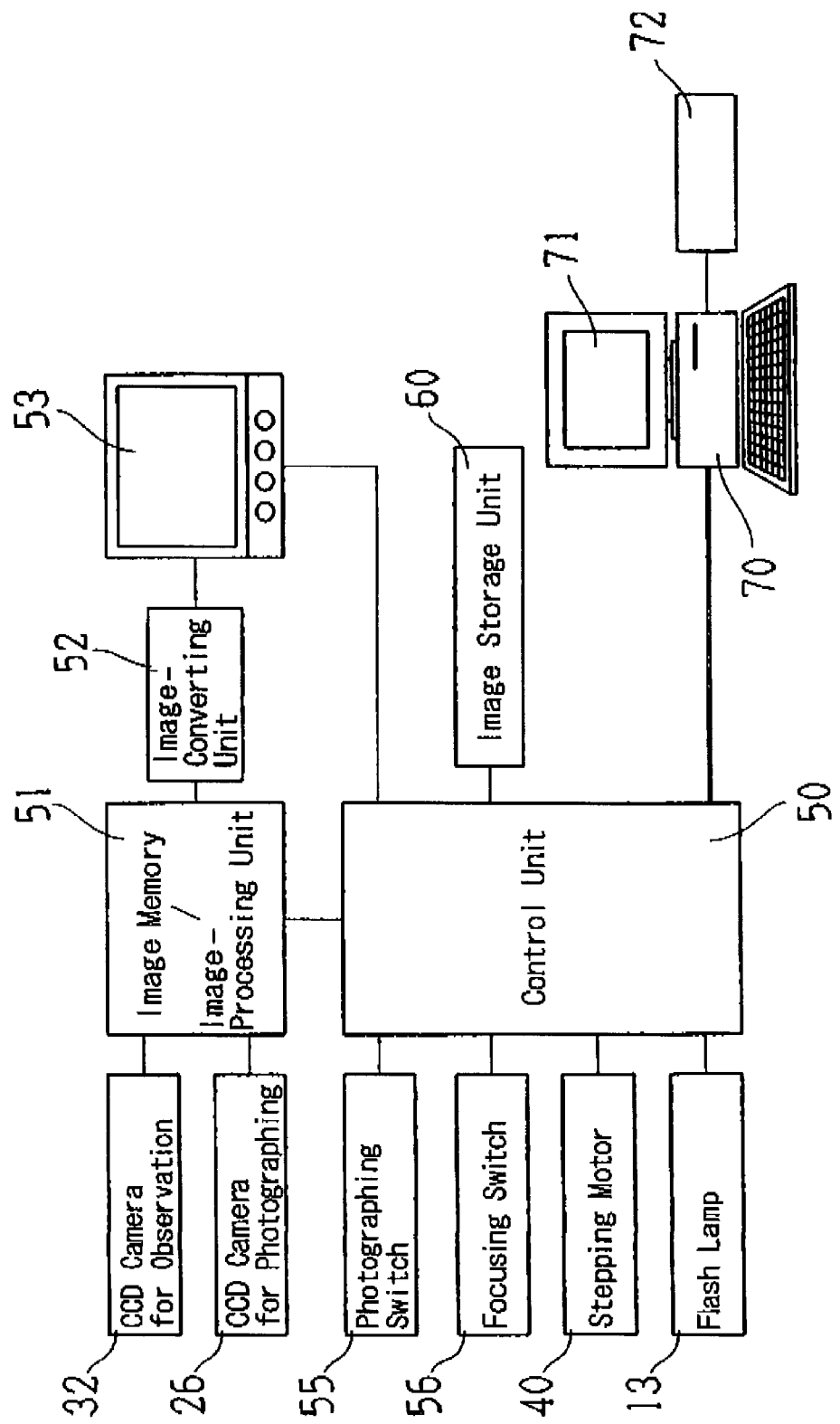
FIG. 3 is a view showing a schematic configuration of primary units of a control system of the fundus camera consistent with the preferred embodiment of the present invention.

Next, as to a fundus camera having the above-mentioned structure, a description of functions of primary units in a control system of the fundus camera will be given referring to FIG. 3 showing a schematic configuration of the system.

First, as preparation for photographing the eye E, an alignment between the eye E and the optical system of the apparatus (fundus camera) is performed. The optical system stored in a casing is put on a movable base, and it makes a relative movement to a fixed base by a sliding mechanism, which is not indicated in the figure. After the head of an examinee is fixed on a chin rest disposed on the fixed base, the eye E is illuminated by infrared illumination light by turning on the lamp 10. Infrared reflection light from the fundus Ef is reflected by the dichroic mirror 25, and an image of the eye E is photographed by the camera 32. After converted from analog to digital, picture signals from the camera 32 are inputted to an image memory/image-processing unit 51 and an image-converting unit 52 for converting those picture signals to picture signals for the LCD display, and then to the LCD 53, which is a liquid crystal display, whereby the image of the eye E is displayed thereon. While observing the image of the eye E (a monochrome image at this point) shown on the LCD 53, the examiner observes an alignment reflex formed by an alignment optical system not shown in the figure (for example, the alignment optical system may be structured by disposing the edges of a pair of right and left optical fibers emitting infrared light in front of the diaphragm 22) in order to perform an alignment for adjustment of the working distance between the eye E and the optical system and for adjustment of the optical axes.

After completing the alignment, the examiner moves the lens 23 by operating a focusing switch 56 so that the photographing surfaces of the cameras 26 and 32 are placed at conjugate positions with the fundus Ef. A control unit 50 rotates the motor 40 in accordance with an operational signal of the switch 56 and moves the lens 23 along the optical axis. This operation is done to correct the gap in a focus position derived from a refractive error of the eye E, to adjust the focus to the fundus Ef, and to form a clear image of the fundus Ef. As mentioned before, as the visible light emitted from the fixation light 36 is reflected by the dichroic mirror 25 and projected onto the fundus Ef, the visible light can be clearly recognized due to correction of a refractive error of the eye E, and then the examines can fixate his eye to the light emitted from the fixation light 36.

An image of a focus index (an image on an index plate 47) photographed by the camera 32 along with an image of a fundus Ef by the camera 32 is utilized for adjusting the focus by moving the lens 23. While observing the infrared fundus image and the image of the focus index photographed by the camera 32 and displayed on the LCD 53, the examiner operates the switch 56 to adjust the focus of the image of the focus index. By doing this operation, it is possible to, correct the gap with a focus position derived from the refractive error of the eye E. At this stage, the control unit 50 obtains a travel position (a movement amount) by recognizing the number of rotary pulses of the motor 40 and converts it into diopters indicating a refractive degree and displays on the LCD 53. The display of the diopter may be a guideline for the examiner to note a degree of the refractive error of the eye E. When the degree of the refractive error is already known, a moving direction of the lens 23 is easily recognized, and the focus of the fundus image is easily adjusted by comparing the known degree and the information displayed on the LCD 53. Further, the fixation light 36 can be used in a manner that the examinee can easily and clearly recognize it from the start.

In order to change the part of the fundus Ef to be photographed, the fixation light 36 is moved in a preferred direction by operating the adjustment knob 37. When the camera 32 is used to photograph an image of the fixation light 36, the examiner can easily recognize where to move the fixation light 36 because the image of the fixation light 36 is shown along with the fundus image on the LCD 53.

After completing adjustment of the focus to observe an image of the fundus Ef to be photographed, the examiner generates a trigger signal by pressing a photographing switch 55. In response to input of the trigger signal, a control unit 50 causes the firing (lighting) to the lamp 13 in order to illuminate the fundus Ef with visible illumination light. Visible reflection light from the fundus Ef enters the camera 26 as it proceeds along the optical path mentioned above. Picture signals from the camera 26 are inputted to the image memory/image-processing unit 51, and a still picture is stored in the image memory/image-processing unit 51 in synchronism with the firing (lighting) of the lamp 13.

After the picture signals sent from the image memory/image-processing unit 51 are changed into an image photographed by the camera 26 under control by the control unit 50, the photographed image is inputted into the LCD 53 via the image-converting unit 52, and the image of the fundus Ef is shown in color on the LCD 53.

An image storage unit 60, such as an MO (a magneto-optical disk) and/or a memory card, for storing a large amount of image data is connected to the control unit 50 so that the image storage unit 60 can preserve the photographed image stored in the image memory/image-processing unit 51. It is possible that the image data stored in the image memory/image-processing unit 51 and the image storage unit 60 are output and sent to an external computer 70 connected thereto with a communication cable, so that the image of the fundus Ef is freely displayed and observed on a display 71 connected to the computer 70, and that the image is printed out by a printer 72. For example, when a memory card is used as the image storage unit 60, the computer 70 reads in the data stored in the memory card and sends them out to display the image of the fundus on the display 71, and to print it out by using the printer 72.

As explained above, according to the present invention, it is possible to simplify a unit mechanism and to dispose an internal fixation light at a suitable position for efficiently guiding a sight line.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye to be examined, the camera comprising:

an illumination optical system for illuminating the fundus of the eye with visible illumination light for photographing and with invisible illumination light for observation;

a photographing optical system including a first photographic element having a sensitivity to a visible wavelength range, for photographing an image of the fundus with visible reflection light from the fundus;

an observation optical system including
      a first wavelength-selecting mirror having a wavelength-selecting property of reflecting approximately all of an invisible wavelength range and a small part of the visible wavelength range and transmitting a large part of the visible wavelength range, disposed on a first optical path of the photographing optical system, and
      a second photographic element having a sensitivity to the invisible wavelength range, disposed on a second optical path divided from the first optical path by the first wavelength-selecting mirror, for photographing an image of the fundus with invisible reflection light from the fundus; and a fixation target projection optical system including a fixation light source for emitting visible fixation target light, disposed on a third optical path divided from the second optical path by a light-dividing member, wherein the visible fixation target light is reflected by the first wavelength-selecting mirror and is delivered to the eye.

2. The fundus camera according to claim 1, further comprising a moving unit which moves the fixation light source within a plane vertical to an optical axis of the third optical path.

3. The fundus camera according to claim 1, wherein the illumination optical system includes:

a visible illumination optical system including a first light source, for illuminating the fundus with the visible illumination light; and an invisible illumination optical system including a second light source, for illuminating the fundus with the invisible illumination light.

4. The fundus camera according to claim 3, wherein the second light source includes a lamp emitting white illumination light, and the invisible illumination optical system further has an infrared transmission filter and illuminates the fundus with infrared illumination light.

5. The fundus camera according to claim 3, further comprising a second wavelength-selecting mirror disposed on the optical paths of the visible illumination optical system and the invisible illumination optical system for making them coaxial, wherein the second wavelength-selecting mirror has a wavelength-selecting property of transmitting either the invisible wavelength range or the visible wavelength range and reflecting the other.

6. The fundus camera according to claim 1, wherein the first wavelength-selecting mirror has the wavelength-selecting property of transmitting approximately 80% to 90% of the visible wavelength range and reflecting approximately 20% to 10% of the visible wavelength range.

* * * * *

UNITED STATES PATENT AND TRADEMARK OFFICE
CERTIFICATE OF CORRECTION

PATENT NO.    : 6,669,339 B2
DATED         : December 30, 2003
INVENTOR(S)   : Tsuguo Nanjo It is certified that error appears in the above-identified patent and that said Letters Patent is hereby corrected as shown below:

Title page,
Item [75], Inventors, delete "Nanjyo" should read -- Nanjo --.

Signed and Sealed this

Fourth Day of May, 2004

JON W. DUDAS
*Acting Director of the United States Patent and Trademark Office*